US006750660B2

(12) United States Patent
Dickerman et al.

(10) Patent No.: US 6,750,660 B2
(45) Date of Patent: Jun. 15, 2004

(54) APPARATUS FOR EVALUATING DATA REPRESENTING THE ELECTRICAL CHARACTERISTICS OF A COMBUSTION VESSEL

(75) Inventors: Robert L. Dickerman, Northfield, MA (US); Terry M. Grayson, Granby, CT (US)

(73) Assignee: Alstom Technology Ltd, Baden (CH)

( * ) Notice: Subject to any disclaimer, the term of this patent is extended or adjusted under 35 U.S.C. 154(b) by 288 days.

(21) Appl. No.: 09/950,959

(22) Filed: Sep. 12, 2001

(65) Prior Publication Data

US 2003/0048830 A1 Mar. 13, 2003

(51) Int. Cl.$^7$ .............................................. G01R 27/08
(52) U.S. Cl. ...................................... 324/691; 324/705
(58) Field of Search ............................... 324/691, 705, 324/158.1, 510, 511, 627, 628, 661, 205; 361/42, 263

(56) References Cited

U.S. PATENT DOCUMENTS

| | | | |
|---|---|---|---|
| 4,126,830 A | * 11/1978 | Schade, Jr. ................. | 330/277 |
| 4,656,595 A | 4/1987 | Hognestad | |
| 4,914,378 A | 4/1990 | Hayashi et al. | |
| 5,493,246 A | * 2/1996 | Anderson .................... | 327/382 |
| 6,201,479 B1 | * 3/2001 | Zydek et al. ............... | 340/664 |
| 6,249,122 B1 | * 6/2001 | Vail et al. ................... | 324/368 |
| 2003/0025514 A1 | * 2/2003 | Benes ......................... | 324/713 |

FOREIGN PATENT DOCUMENTS

| | | |
|---|---|---|
| EP | 0 277 467 | 10/1988 |
| WO | WO 01/94876 | 12/2001 |

OTHER PUBLICATIONS

PCT International Search Report dated Sept. 24, 2003.
Horowitz P and Hill W.: "The Art of Electronics" Cambridge University Press, Cambridge, XP002246138, ISBM: 0–521–37095–7 –See argumentation against the unity of the application –pp. 223–224.

* cited by examiner

*Primary Examiner*—N. Le
*Assistant Examiner*—Walter Benson
(74) *Attorney, Agent, or Firm*—Russell W. Warnock

(57) ABSTRACT

An apparatus for evaluating data representing the electrical characteristics of a combustion vessel, the combustion vessel being operable to combust a fuel. The apparatus includes a matrix of nodes 132 arranged on an ohmic material of the combustion vessel, a wire 116A, 116B, 118A, 118B, connected to each respective node 132 and a switch SW1, SW2 connected to each wire and to a current source. A circuit 110A, 110B for reducing leakage currents uses an added series element, optimally a diode D1, and feedback control of the voltage across the diode to a set point of zero volts to effectively reduce the off-state leakage current of each switch SW1, SW2.

5 Claims, 5 Drawing Sheets

APPARATUS FOR EVALUATING DATA REPRESENTING THE ELECTRICAL CHARACTERISTICS OF A COMBUSTION VESSEL

BACKGROUND OF THE INVENTION

The present invention relates to an apparatus for evaluating data representing the electrical characteristics of a combustion vessel, the combustion vessel being operable to combust a fuel.

An apparatus to evaluate data representing the electrical characteristics of a combustion vessel of the type which combusts a fuel may include a matrix of nodes arranged on an ohmic material of the combustion vessel and a wire connected to each respective node. Additionally, such an apparatus may include an electrical switch connected to each wire and to a current source.

All electrical switches have leakage currents associated with their off-states. Semi-conductor switches typically have higher leakage currents than electro-mechanical switches. One of the steps in the process of switch selection is to determine whether the off-state leakage current is sufficiently low for the application. If it is not, then either a different switch must be used or a means of reducing the leakage current must be devised. As an example, when using the four terminal ohmmeter method for measuring electrical resistivity or conductivity of a sheet material which has a varying resistivity across its area, multiple contacts to the material must be made, with the contacts typically arranged in a grid. At each measurement site, one microvolt meter or one current source connection may be made. To automate the measurement, electronic switches may be used for connecting the volt meter and current source to multiple fixed sheet contacts. In a system with hundreds or thousands of contacts, it is desirable to use only a single wire with each contact point in order to reduce wiring costs.

The single wire must carry either the excitation current, or provide a microvolt meter connection, or make no connection. If the current source switch associated with a particular wire is intended to be off and that wire is being used by the microvolt meter to sense voltage, the off-state leakage current of the switch will cause a significant voltage to develop in the wire's finite resistance. The result will be that an error voltage is added to the desired voltage measurement. Even if double wires were used, in commercial applications such as characterization of boiler water walls, the excitation and measurement circuits would still share insulation pin resistance which could range from 3–6 mΩ. The magnitude of the leakage currents may be highly variable, depending on temperature, switch voltage, and the age of the switch, so the error voltages cannot be easily measured and subtracted.

SUMMARY OF THE INVENTION

It is one object of the present invention to provide an apparatus for evaluating data representing the electrical characteristics of a combustion vessel, the combustion vessel being operable to combust a fuel. According to one preferred aspect of the present invention, the apparatus includes a matrix of nodes arranged on an ohmic material of the combustion vessel, at least one wire connected to a respective node, and a switch. The switch is connected to the at least one wire and to a current source for controlling the delivery of a current to the respective node via the switch and the at least one wire and the switch has an on state and an off state, the off state allowing a leakage current through the switch. Also, the apparatus includes means for preparing a data set based on voltage data gathered from the matrix of nodes arranged on an ohmic material of the combustion vessel including calculating the resistivity of the ohmic material by iteratively imposing a known current to the matrix and measuring voltage at the nodes, each the iteration of imposing a known current resulting in a set of measured voltages. The apparatus further includes a circuit for reducing leakage currents in the switch that controls delivery of current to a load. The circuit includes a series component positioned between the switch and the load, the series component permitting delivery of current to the load through the switch and across which series component the leakage current develops a voltage and an active device connected across the series component to force the voltage across the series component to zero volts by means of feedback control, whereby the leakage current is reduced to an input current of the active device.

It is a further object of the invention to provide a new and improved circuit for reducing leakage currents in high current switches. This is accomplished by incorporating an operational amplifier and series diode between the load and the switch. The operational amplifier is configured to force the voltage across the series diode to zero volts, thereby reducing the current through the diode to zero. Since the load then "sees" only a connection to the series diode and a connection to the operational amplifier, the inventive circuit replaces the leakage current of the original switch with the input current of the operational amplifier. The operational amplifier typically has a much smaller input current than the typical leakage current of high current switches and also has very small input offset voltage. Since the bias currents of the amplifier are smaller than the leakage currents of the high current switch, the voltage errors associated with the amplifier's bias currents are proportionately smaller. In addition, the input current to the operational amplifier is more stable and easily accounted for in any measurement scheme.

The circuit effectively reduces leakage currents associated with the off-state of high current switches such as power MOSFETs (metal oxide semiconductor field effect transistors). The circuit may be used with any type of semiconductor, electrical or electro-mechanical switch. The circuit has applications in many areas, including the making of multiple sheet resistivity measurements.

DETAILED DESCRIPTION OF THE PREFERRED EMBODIMENTS

Figure 1:
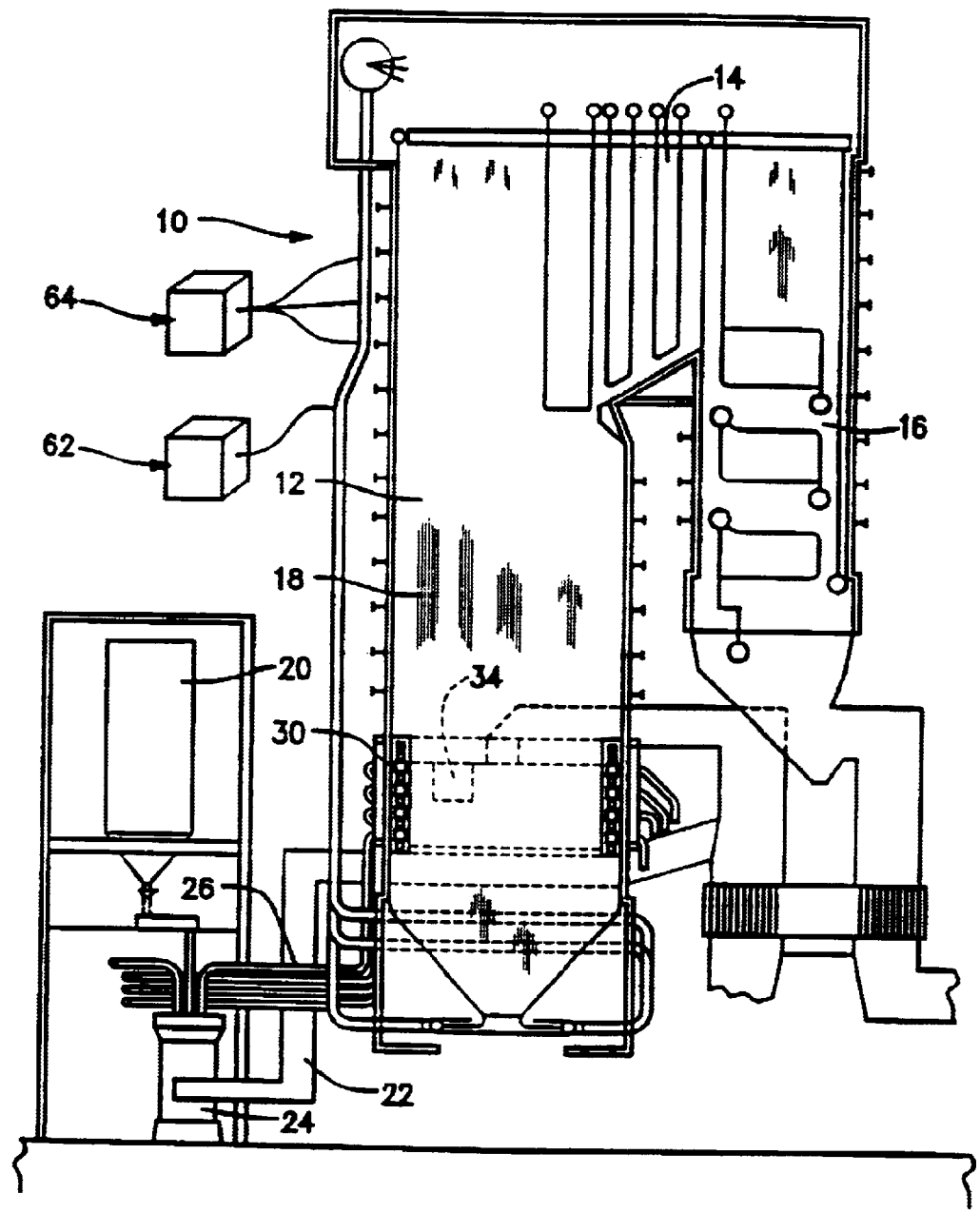
FIG. 1 is a schematic sectional view of a combustion vessel comprising a fossil fuel fired furnace and operable in accordance with the method of the present invention.

FIG. 1 illustrates an exemplary power generating unit 10 having a fossil fuel fired combustion vessel in the form of a furnace 12 and additionally including a horizontal gas pass 14 and a back pass 16. The furnace 12 has a fireside delimited by water walls 18 each having a plurality of water wall tubes 28, shown in FIG. 3, in which a heat exchange medium—namely, water—is circulated and which is converted into steam as a result of heating of the tubes 28 during the combustion of a fossil fuel such as, for example, coal, in the furnace 12. The power-generating unit 10 may include other conventional elements such as, for example, a turbine (not illustrated) for generating electricity under the motive action of steam passed thereover. Moreover, the horizontal gas pass 14 and the back pass 16 may comprise selected arrangements of economizers, super heaters and reheaters.

A coal feed apparatus 20 is operable to feed coal to a feeder which controls the rate of coal flow to a pulverizer 24. Hot primary combustion air is also fed to the pulverizer 24 via a duct 22 and this air carries pulverized coal through and out of the pulverizer 24 and thereafter through coal pipes 26 to several groups of coal nozzles. Each group of coal nozzles is mounted in a respective tangential firing windbox 30 that also each support a group of secondary air nozzles. The windboxes 30 introduce controlled flows of air and pulverized coal into the furnace 12 to effect the formation therein of a rotating fireball. The rotating fireball is a combustion process of the type which results in the release of material that contributes to depositions on the fireside surfaces of the water wall tubes 28. Carbon based combustion by-product builds up as slag and/or ash on the fireside surfaces of the water wall tubes 28.

Certain combustion vessels, such as those fired by natural gas, do not corrode or waste in the manner of a combustion vessel fired by coal or solid waste. Therefore, the area of a segment of a combustion vessel wall between nodes in a natural gas fired combustion vessel, as compared to a segment of a combustion vessel wall of a fossil fuel-fired combustion vessel, will remain substantially constant over time. As a result, fluctuations in measured voltages in a natural gas fired combustion vessel will be substantially related to the increased resistance of the segment resulting from temperature changes. In calculations for this type of combustion vessel, i.e., natural gas fired, the area of the segment between nodes is known and the resulting fluctuations in the calculated resistance of the segment can be transformed according to known relationships into an accurate measure of the temperature of the segment.

On the other hand, in a solid waste or coal fired combustion vessel, corrosion or wastage of the walls of the combustion vessel occurs with relatively more regularity as compared to natural gas fired combustion vessels. Under such conditions, both the temperature and the area of the evaluated segment of combustion vessel produce changes in measured voltage between nodes. Under these circumstances, the temperature must be measured separately to eliminate multiple variables in the calculations. Following compensation for changes in temperature (which are known), changes in calculated resistances are attributable to changes in the cross-sectional area, e.g., thickness, of the evaluated portion of the combustion vessel.

Figure 2:
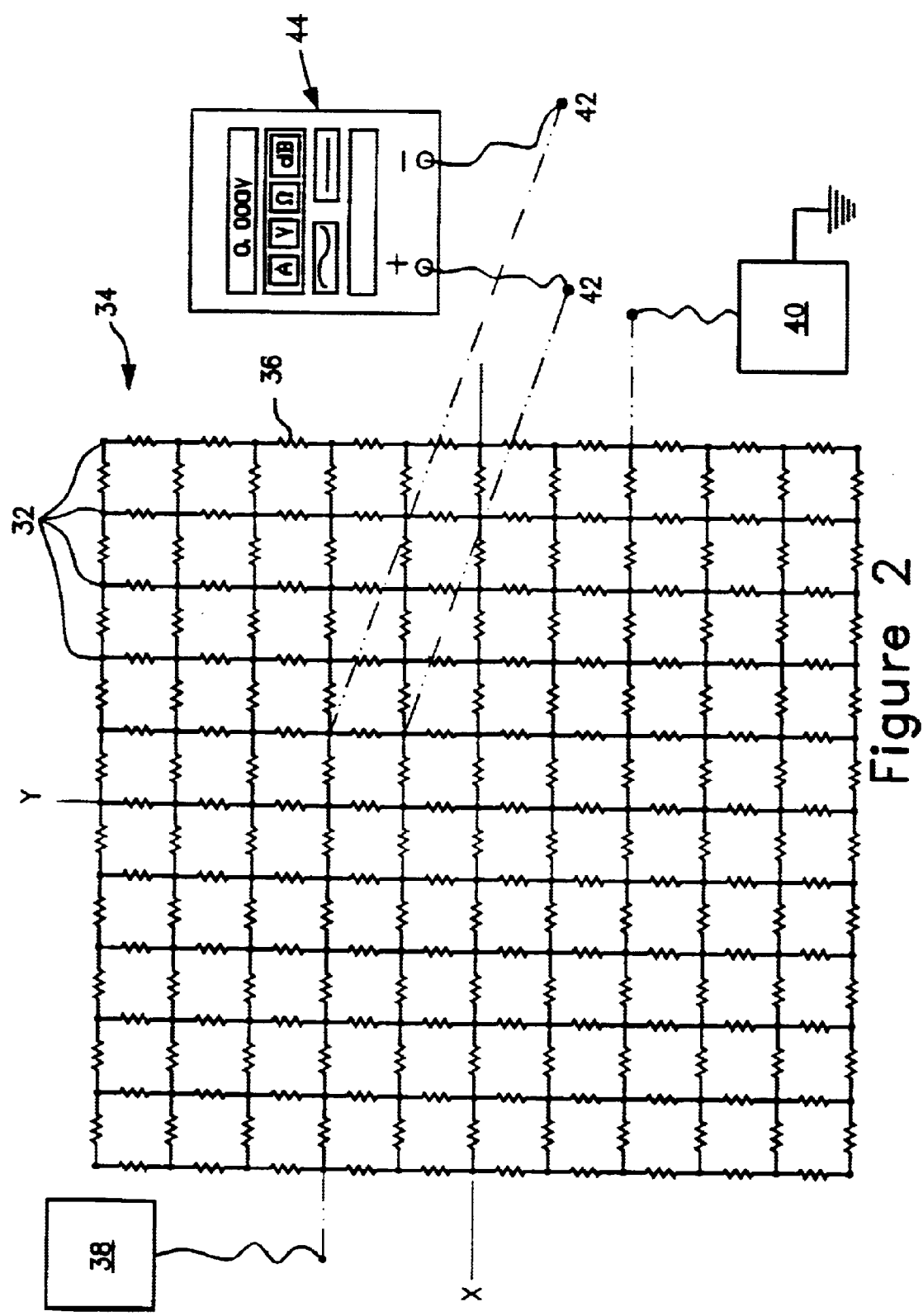
FIG. 2 is a schematic view of a matrix of nodes which could hypothetically be arranged on a portion of interest of a wall of a combustion vessel for supplying data in accordance with the method of the present invention.

FIG. 2 is a schematic representation of a plurality of nodes 32 forming a matrix 34 which could hypothetically be arranged on a portion of interest of the water wall of a combustion vessel. Segments of a water wall between respective adjacent pairs of the nodes 32 are characterized as unknown resistances 36 which are schematically shown in FIG. 2 as non-linear line segments extending between the respective adjacent pairs of the nodes 32. For the purposes of discussion, the matrix 34 is treated as a two-dimensional surface extending in the X (horizontal) and Y (vertical) directions. The four-wire technique is iteratively utilized to obtain sets of data comprising voltage measurements between nodes 32 in the matrix 34. The four-wire technique applies a source of constant current 38 and a sink 40 (ground) at various locations in the matrix 34. For each iteration of current source/sink, voltage measurements are taken by connecting the leads 42 of a volt meter 44 between nodes 32 in the matrix 34. The resulting sets of voltage measurements are the data from which the values of the unknown resistances 36 are calculated.

Figure 3:
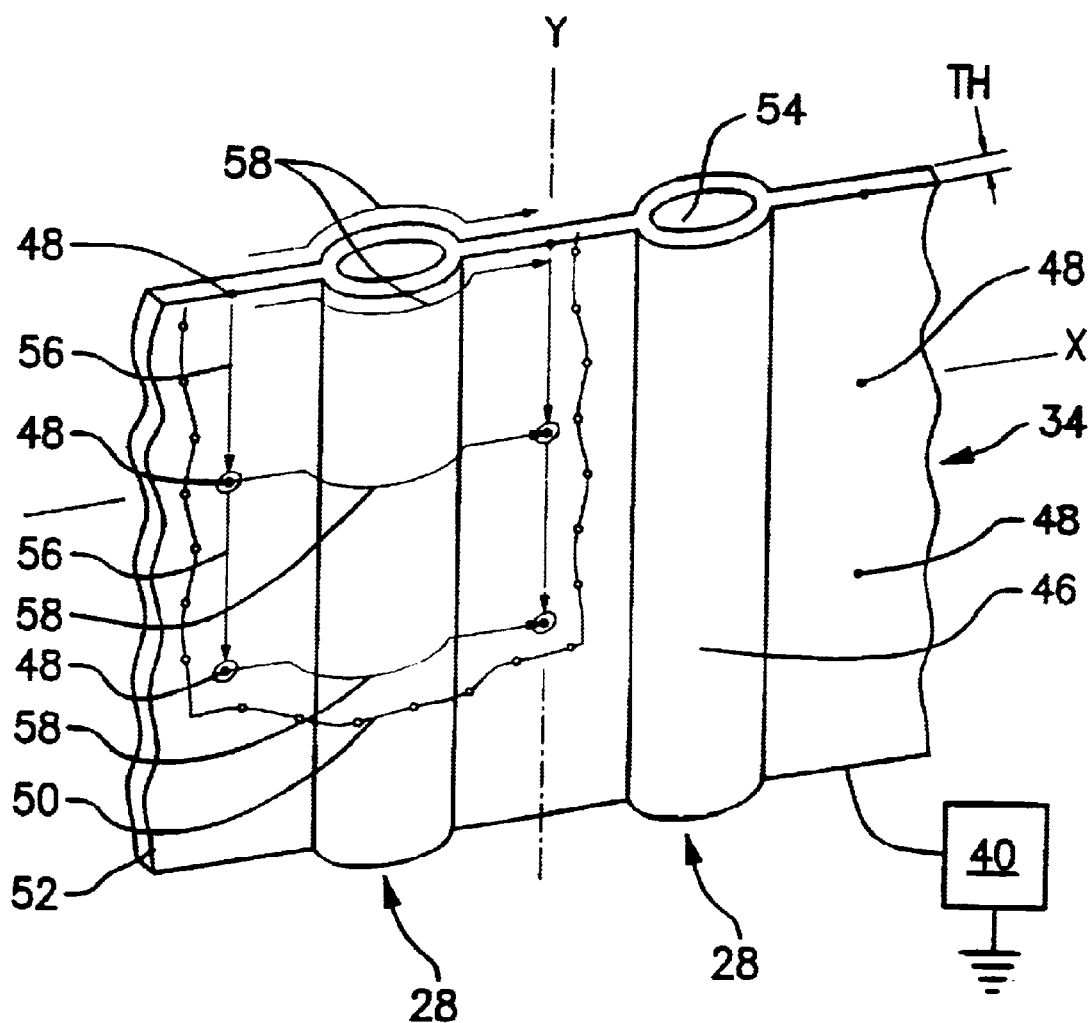
FIG. 3 is an enlarged perspective sectional view of a portion of interest of a waterwall of the combustion vessel shown in FIG. 1.

Calculating the remaining thickness of an ohmic material (e.g., carbon steel) is relatively simple for an isothermal material with uniform cross-section. However, calculating the remaining thickness of an ohmic material comprised in a water wall is relatively more complicated. FIG. 3 shows a portion of interest of a water wall 18 of the furnace 12 shown in FIG. 1. The water wall comprises individual water tubes 28 laid side by side connected by webs of material as illustrated. The water wall 18 has an inner facing surface 46 that faces the interior of the furnace 12. A plurality of nodes 48 form a matrix 50 arranged on the outside surface 52 of the water wall 18 such that these nodes are not directly exposed to the radiation heat and other thermal conditions to which the inner facing surface 46 of the water wall 18 is exposed by virtue of its direct exposure to the combustion of fossil fuel in the furnace 12. For example, the inner facing surface 46 of the water wall 18 can be exposed to temperatures up to 900° C. (900 degrees C.). The nodes 48 need not be in the form of additional physical structures on the water wall 18 but can, instead, be arbitrarily designated locations on the water wall. The nodes 48 are locations on the water wall 18 schematically shown as circles. The matrix 50 can be any arbitrarily designated arrangement of nodes 48 and need not be physically delimited by any defined structure of the water wall 18. Thus, the matrix 50 is schematically shown in FIG. 3 in broken lines. The water tubes 28 in the illustrated embodiment are oriented generally parallel to the Y axis and include an interior surface 54. Nodes 48 are, for purposes of calculation, effectively equidistantly spaced from one another in the X and Y directions forming a two dimensional matrix, whereby the term "effectively equidistantly spaced" is to be understood as encompassing both the situation in which the respective nodes of adjacent pairs of the nodes 48 are at a uniform spacing from one another as well as the situation in which the nodes 48 are not physically equidistant from one another but their relationships can be mathematically adjusted so that, for purposes of calculation, they behave as equidistantly spaced nodes as discussed below.

Current from constant current source 38 entering at the upper left-hand node has a simple path 56, schematically shown by arrows in FIG. 3, parallel to the Y axis. Current flow parallel to the X axis takes a relatively more complicated path 58, schematically shown by arrows in FIG. 3. Thus, the sheet resistivity of the water wall parallel to the X axis will be different from the sheet resistivity of the water wall parallel to the Y axis. However, this fact can be compensated for by establishing the ratio R of the sheet resistivity parallel to the Y axis to the sheet resistivity parallel to the X axis. This relationship is consistent enough over a range of time and temperature so that it does not unduly effect the resulting calculations. The calculated resistances are ultimately used to determine the thickness TH or temperature of the portion of the water wall being evaluated.

Figure 4:
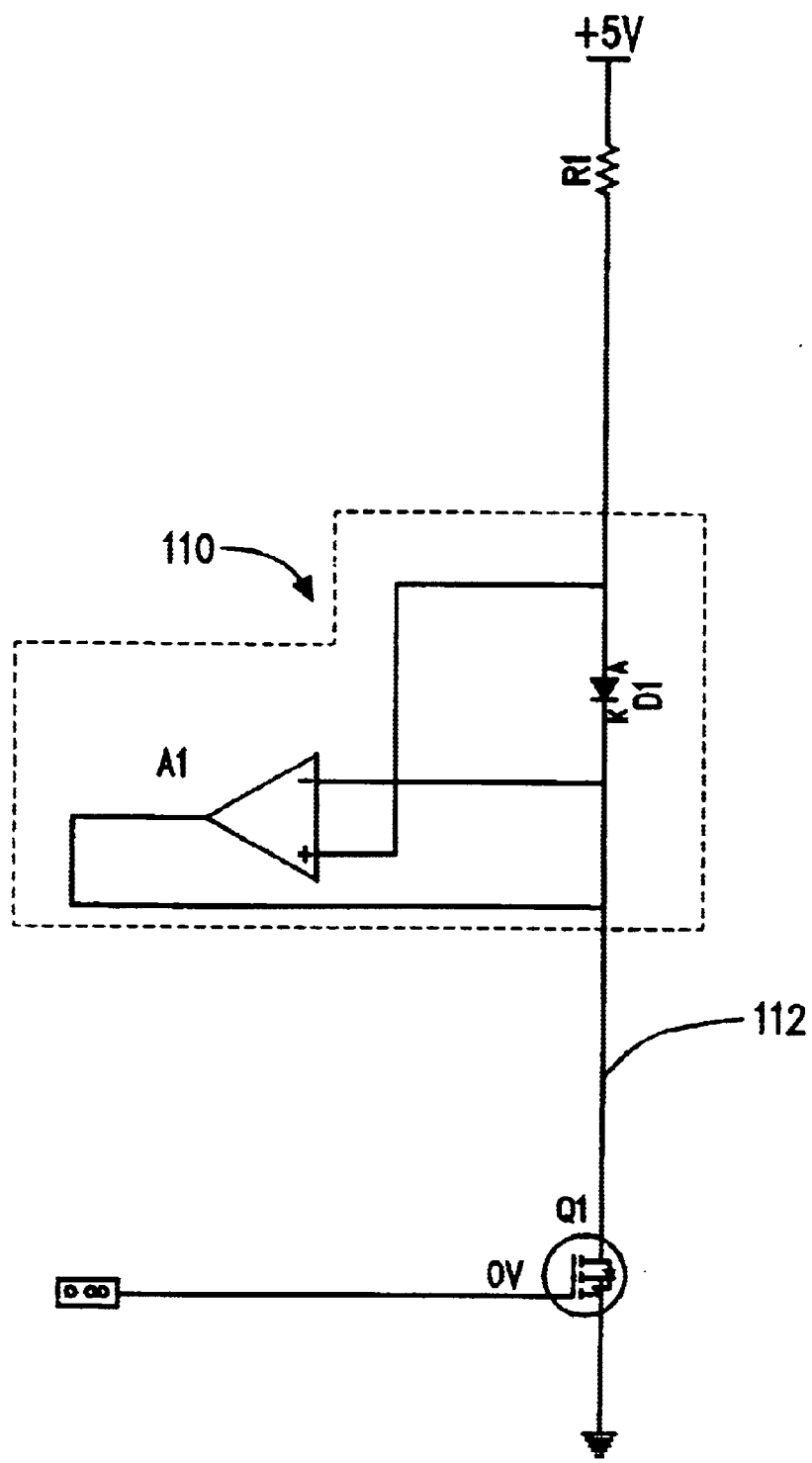
FIG. 4 is a schematic diagram of a circuit for reducing leakage currents in high current switches in series with an electronic switch in accordance with the present invention.
Figure 5:
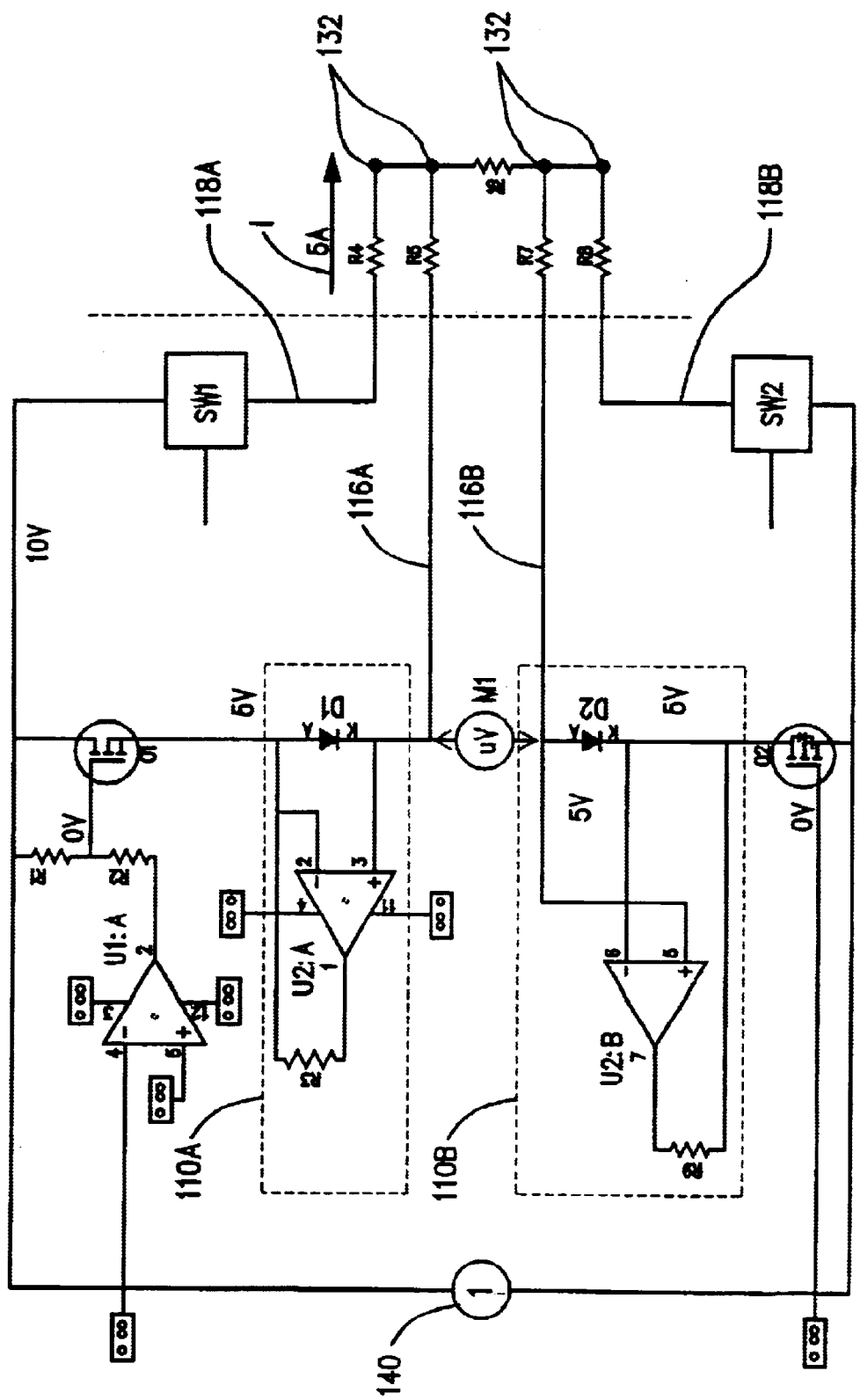
FIG. 5 is a schematic diagram of a pair of circuits for reducing leakage currents in high current switches in accordance with the present invention connected between a load and a corresponding pair of high current switches.

Reference is now had to FIGS. 4 and 5 in which an electronic circuit for reducing leakage currents in high current switches is generally designated by the numeral 110.

The circuit can be deployed to improve the performance of a resistance measurement arrangement, such as the resistance measurement arrangement comprising the nodes 32 and the matrix 34 described hereinabove with respect to FIGS. 2 and 3. FIG. 4 shows that the circuit for reducing leakage currents 110 is connected in series between a high current MOSFET switch Q1 and a load represented by resistance R1. In this configuration the circuit for reducing leakage currents 110 effectively reduces the off-state leakage current that will flow through MOSFET switch Q1 to the load represented by resistance R1.

Under ideal circumstances, the load represented by R1 will have zero volts across it when the MOSFET switch is off. The only way this can be true is to reduce the current flow through load represented by resistance R1 to zero. This is accomplished in the circuit for reducing leakage currents 110 by the illustrated configuration of a diode D1 and operational amplifier A1 connected between the load represented by resistance R1 and the power MOSFET switch Q1. Operational amplifier A1 is connected in such a way that it draws current out of or forces current into the node connected to the drain of the power MOSFET switch Q1. The operational amplifier A1 supplies current to the extent that is necessary to generate a "virtual short" between the positive and negative input terminals of the operational amplifier A1, i.e., to force the voltage across D1 to 0.000 volts (1/1000 volts). In other words, operational amplifier A1 is used to supply the leakage current required by MOSFET switch Q1 instead of allowing the leakage current to flow through the load represented by resistance R1. The current/voltage characteristic of diode D1 requires that the current through it be zero when the voltage across it is zero. Therefore, the current through the load represented by resistance R1 when MOSFET switch Q1 is off is limited to the operational amplifier input current.

The circuit illustrated in FIG. 4 can reduce the off-state current flow through the load represented by resistance R1 by several orders of magnitude. This is so because the load represented by resistance R1 will respond as if there were only a connection to the diode and the input current needed for the operational amplifier—in other words, the load represented by resistance R1 will "see" only a connection to the diode and the input current needed for the operational amplifier A1. Operational amplifiers are readily available which have input currents measured in units of pA or $10^{-12}$ Amperes (1/100,000,000,000 Amperes). A typical MOSFET power switch such as the MOSFET switch Q1 typically has an off-state leakage current measured in units of mA or $10^{-3}$ Amperes (1/1,000 Amperes). The result is a reduction in off-state leakage current from a magnitude of $10^{-3}$A (1/1,000 A) to off-state leakage current $10^{-12}$ (1/100,000,000,000 A). In addition, input current to the operational amplifier may be more consistent over time and temperature than the off-state leakage current of a MOSFET switch which varies with temperature and usage. It is easier to account for the more consistent operational amplifier input current, thereby further increasing the accuracy of measurement circuits incorporating the circuit for reducing leakage currents 110.

A practical application of the circuit for reducing leakage currents will now be described with reference to FIG. 5. FIG. 5 is a schematic representation of an electronic apparatus for implementing the four terminal ohmmeter method for measuring electrical resistivity of a water wall of a combustion vessel and can be deployed, for example, in cooperation with the resistance measurement arrangement comprising the nodes 32 and the matrix 34 described hereinabove with respect to FIGS. 2 and 3. A suitable water wall in connection with which the circuit shown in FIG. 5 could be deployed could be, for example, the water wall 18; in FIG. 5, an exemplary water wall of a combustion vessel in the form of a boiler which combusts pulverized coal is represented by contact nodes 132 and a particular portion of the water wall to be evaluated is represented by resistance R6. Single wires 116A, 116B, 118A, 118B are connected to each contact point or node 132. The single wires carry alternately an excitation current or provide a microvolt meter connection or make no connection. In FIG. 5, wire 118A is connected to a current source 140 through switch SW1. Wire 118B connects to the other terminal of the current source through switch SW2.

In one possible operational scenario in which switches SW1 and SW2 are on and a current I is flowing from current source 140, through wire 118A, the water wall as electrically characterized or represented by resistance R6, through wire 118B, and back to the current source 140. MOSFET switches Q1 and Q2 are arranged to alternately provide a current source and sink, respectively, through wires 116A and 116B when in the on-state, or, when in the off-state, ideally provide no current. Circuits for reducing leakage currents 110A and 110B are connected between the water wall and switches Q1 and Q2 respectively. Resistances R4, R5, R7 and R8 represent the series resistance of iron voltage sensing wire attached to the nodes 132 on the boiler water wall. In this configuration microvolt meter M1 is connected across resistance R6 via wires 116A and 116B to measure the voltage drop across resistance R6. Any leakage currents through switches Q1 and Q2 would impair the accuracy of the measurement by causing an unknown voltage to develop across resistances R5 and R7 as described above.

Circuits for reducing leakage currents 110A and 110B effectively reduce the leakage currents through MOSFET switches Q1 and Q2 to the input current of the operational amplifiers U2A and U2B. MOSFET Q1 is a P channel MOSFET while MOSFET Q2 is an N channel MOSFET. In this embodiment, the connections are arranged so that low-impedance sources, with respect to the waterwall, constitute the setpoint signals for the two control loops. The setpoint signals are nominally zero volts with respect to the waterwall, and are applied at a positive operational amplifier input in both loops. Therefore, the connections of operational amplifier U2A are reversed on the diode but perform exactly the same function as operational amplifier U2B. Resistors R3 and R9 connected to the operational amplifier outputs are a practical refinement, to reduce power dissipation in the operational amplifiers when transistors Q1 and Q2 are turned on.

Some adjustments or restrictions may be required to protect the circuit components comprising the circuits for reducing leakage currents 110A, 110B and to ensure feedback control system stability in a practical system. Component selection is important because the performance of the circuit is limited by the input current of the operational amplifier and the input offset voltage of the operational amplifier.

While a preferred embodiment of the foregoing invention has been set forth for purposes of illustration, the foregoing description should not be deemed a limitation of the invention herein. Accordingly, various modifications, adaptations, and alternatives may occur to one skilled in the art without departing from the spirit and the scope of the present invention.

What is claimed is:

1. An apparatus for evaluating data representing the electrical characteristics of a combustion vessel, the combustion vessel being operable to combust a fuel, comprising:

a matrix of nodes arranged on an ohmic material of the combustion vessel;

at least one wire connected to a respective node;

a switch connected to the at least one wire and to a current source for controlling the delivery of a current to the respective node via the switch and the at least one wire, the switch having an on state and an off state, the off state allowing a leakage current through the switch;

means for preparing a data set based on voltage data gathered from the matrix of nodes arranged on an ohmic material of the combustion vessel including calculating the resistivity of the ohmic material by iteratively imposing a known current to the matrix and measuring voltage at the nodes, each the iteration of imposing a known current resulting in a set of measured voltages; and a circuit for reducing leakage currents in the switch that controls delivery of current to a load, the circuit including:

a series component positioned between the switch and the load, the series component permitting delivery of current to the load through the switch and across which series component the leakage current develops a voltage, and an active device connected across the series component to force the voltage across the series component to zero volts by means of feedback control, whereby the leakage current is reduced to an input current of the active device.

2. An apparatus according to claim 1, wherein the active device is an operational amplifier and the series component is a diode.

3. An apparatus according to claim 2, wherein the operational amplifier supplies the leakage current required by the switch, whereby the load sees only the input current of the operational amplifier.

4. An apparatus according to claim 3, wherein the diode has a current/voltage characteristic requiring that the current through the diode be zero when the voltage across the diode is zero.

5. A circuit for reducing leakage current through an electrical switch, the circuit comprising:

series component means for passing current supplied from the switch, the current developing a voltage across the series component; and feedback control means for forcing the voltage across the series component means to zero volts, whereby the leakage current of the switch is replaced by an input current of the feedback control means and the series component means is a diode having a current/voltage characteristic requiring that a current through the diode be zero when the voltage across the diode is zero.

* * * * *